(12) United States Patent
Casavant et al.

(10) Patent No.: US 7,218,965 B2
(45) Date of Patent: May 15, 2007

(54) PREFERRED ADI/R: A PERMANENT PACING MODE TO ELIMINATE VENTRICULAR PACING WHILE MAINTAINING BACKUP SUPPORT

(75) Inventors: David Casavant, Reading, MA (US); Paul Belk, Maple Grove, MN (US); Thomas J. Mullen, Ham Lake, MN (US); John C. Stroebel, Blaine, MN (US)

(73) Assignee: Medtronic, Inc., Minneapolis, MN (US)

( * ) Notice: Subject to any disclaimer, the term of this patent is extended or adjusted under 35 U.S.C. 154(b) by 339 days.

(21) Appl. No.: 10/755,454

(22) Filed: Jan. 12, 2004

(65) Prior Publication Data

US 2004/0143299 A1 Jul. 22, 2004

Related U.S. Application Data

(63) Continuation of application No. 10/246,816, filed on Sep. 17, 2002, which is a continuation-in-part of application No. 09/413,571, filed on Dec. 21, 2000, now Pat. No. 6,772,005.

(51) Int. Cl.
*A61N 1/368* (2006.01)
(52) U.S. Cl. .......................................................... 607/9
(58) Field of Classification Search ................ 600/373, 600/374, 393, 508, 509, 515, 516, 518, 519, 600/521, 522; 607/4, 5, 9, 14, 116, 119, 607/122, 123
See application file for complete search history.

(56) References Cited

U.S. PATENT DOCUMENTS 3,057,356 A 10/1962 Greatbatch
3,253,596 A 5/1966 Keller
3,478,746 A 11/1969 Breatbatch
3,595,242 A 7/1971 Berkovits
3,648,707 A 3/1972 Greatbatch
3,747,604 A 7/1973 Berkovits
4,312,355 A 1/1982 Funke
4,428,378 A 1/1984 Anderson et al.
4,476,868 A 10/1984 Thompson
4,523,593 A 6/1985 Rueter et al.
4,856,523 A 8/1989 Sholder et al.
4,890,617 A 1/1990 Markowitz et al.
4,932,046 A 6/1990 Katz et al.
5,052,388 A 10/1991 Sivula et al.
5,318,594 A 6/1994 Limousin et al.
5,345,362 A 9/1994 Winkler (Continued)

FOREIGN PATENT DOCUMENTS

| EP | 0448193 | 9/1991 |
|---|---|---|
| EP | 0830877 | 3/1998 |
| WO | 9532758 | 12/1995 |
| WO | 02051499 | 7/2002 |

*Primary Examiner*—Robert E. Pezzuto
*Assistant Examiner*—Frances P. Oropeza
(74) *Attorney, Agent, or Firm*—Daniel G. Chapik; Girma Wolde-Michael

(57) ABSTRACT

An ADI/R mode is implemented using an intelligent pacing system to continually monitor ventricular response. This ensures AV conduction whenever possible so as to gain all the benefits of cardiac contractile properties resulting from native R-waves. In the event where AV conduction is blocked, the pacing mode is switched to a DDD/R mode to ensure a paced R-wave. Thereafter, subsequent to a completed interval of a P-wave, ADI/R pacing resumes to monitor ventricular response.

48 Claims, 8 Drawing Sheets

U.S. PATENT DOCUMENTS

| | | |
|---|---|---|
| 5,388,586 A | 2/1995 | Lee et al. |
| 5,643,326 A | 7/1997 | Weiner et al. |
| 5,814,077 A | 9/1998 | Sholder et al. |
| 5,861,007 A | 1/1999 | Hess et al. |
| 5,873,895 A | 2/1999 | Sholder et al. |
| 5,954,755 A * | 9/1999 | Casavant ............... 607/28 |
| 6,122,546 A | 9/2000 | Sholder et al. |
| 6,169,918 B1 | 1/2001 | Haefner et al. |
| 6,256,541 B1 | 7/2001 | Heil et al. |
| 6,397,105 B1 | 5/2002 | Bouhour et al. |
| 6,772,005 B2 | 8/2004 | Casavant et al. |

* cited by examiner

PREFERRED ADI/R: A PERMANENT PACING MODE TO ELIMINATE VENTRICULAR PACING WHILE MAINTAINING BACKUP SUPPORT

CROSS-REFERENCE TO RELATED APPLICATION

This patent application is a continuation of prior U.S. patent application Ser. No. 10/246,816, filed Sep. 17, 2002, entitled "PREFERRED ADI/R: A PERMANENT PACING MODE TO ELIMINATE VENTRICULAR PACING WHILE MAINTAINING BACKUP SUPPORT", which is a continuation-in-part of Ser. No. 09/746,571, now U.S. Pat. No. 6,772,005, filed Dec. 21, 2000, entitled "PREFERRED ADI/R: A PERMANENT PACING MODE TO ELIMINATE VENTRICULAR PACING WHILE MAINTAINING BACKUP SUPPORT", both of which are herein incorporated by reference in their entirety.

FIELD OF THE INVENTION

The present invention generally relates to cardiac pacers, and more particularly to a dual chamber rate responsive pacemaker that incorporates a novel ADI/R pacing mode. More particularly, this pacing mode is one that gives preference to atrial pacing and, at the same time, suppresses ventricular pacing wherever possible and provides the DDI/R or DDD/R modes with ventricular pacing only as backup modes.

BACKGROUND OF THE INVENTION

Early pacemakers were asynchronous (VOO) and stimulated the heart at a fixed rate, independent of the patient's underlying cardiac rhythm or metabolic demand. Although such pacers, typified by U.S. Pat. No. 3,057,356 to Greatbatch, provide a ventricular pacing rate sufficient to sustain life, this pacing mode often competed with native ventricular rhythms. Such competition is undesirable.

Subsequently, demand pacemakers (VVI) were developed. This type of pacer interacts with the patient's heart to provide pacing pulses only when spontaneous ventricular activity is absent. U.S. Pat. No. 3,478,746 to Greatbatch demonstrates an example of such a pacer. This form of pacer provides a ventricular sense amplifier for detecting ventricular depolarizations. A ventricular sensed event resets the pacer's V—V timer. The ventricular sensed event also cancels or inhibits the scheduled ventricular stimulus and thus avoids competition with the native ventricular rhythm.

Atrial synchronized pacers (VAT) were developed almost simultaneously with VVI demand pacemakers. This type of pacer paces the ventricle in response to the detected atrial rate of the patient. The VAT pacer, as typified by U.S. Pat. No. 3,253,596 to Keller, provides an atrial sense amplifier for detecting atrial depolarizations. An atrial sensed event starts the pacer's A-V delay timer. When the A-V timer times out, a ventricular stimulus is provided. Conceptually, such a pacer can be considered as a prosthetic conduction pathway that simulates the natural A-V conduction pathways of the heart. One drawback to this form of pacing is the possibility of competing with ectopic ventricular activity. An ectopic ventricular beat (PVC) may be detected in the atrium. In such cases, an AV interval starts and will result in the generation of a ventricular stimulus a short time after the ventricular depolarization. Although such a pacing regimen is considered harmless when the A-V delay is short, it is possible to deliver the pacing stimulus into the vulnerable period of the ventricle, and thereby initiate a ventricular arrhythmia.

Continued development of pacemakers was marked by the invention of the AV sequential pacer (DVI), as disclosed in U.S. Pat. No. 3,595,242 issued to Berkovits. This form of pacer provides for stimulation in both the atria and the ventricles though providing sensing only in the ventricle. In this DVI mode pacer, a ventricular sense event starts both a V-A escape interval and an A-V interval. The pacer delivers an atrial stimulus at the end of the V-A interval and, at the end of the A-V interval, the pacer delivers a ventricular stimulus. If a ventricular sense event occurs during the V-A or A-V time intervals, the pacer will resynchronize to the ventricular sense event and inhibit the delivery of the scheduled ventricular stimulus.

The DDI mode pacer described by U.S. Pat. No. 3,747,604 to Berkovits further includes an atrial sense amplifier to inhibit the atrial stimulus when an atrial sense event occurs during the V-A interval. The atrial sense event does not start and A-V interval; such timing makes this device especially suitable in patients where atrial competition must be avoided.

The atrial synchronized ventricular inhibited or VDD mode pacer, as disclosed in U.S. Pat. No. 3,648,707 issued to Greatbatch has mechanisms for sensing in the atrium and ventricle while providing stimulating pulses only in the ventricle. In operation, the VDD pacer starts and A-V interval on detected atrial activity and provides a ventricular stimulus if one does not occur within the A-V delay. A ventricular sensed event inhibits the scheduled ventricular stimulus and resets the pacer's V—V timer.

The dual sense, dual pace DDD mode pacers, have been described in U.S. Pat. No. 4,312,355 issued to Funke. The DDD pacer addresses many of the shortcomings of the prior art devices. The DDD mode pacer, as described by Funke, has had wide applications. This type of pacer has sense amplifiers for detecting atrial and ventricular events, as well as output pulse circuitry for stimulating both the atrium and the ventricle.

This form of prior art pacer provides timing circuitry to initiate an A-V delay upon the occurrence of an atrial event. If, during the A-V delay period, no spontaneous ventricular event is sensed, the pacer will produce a ventricular stimulus at the conclusion of the A-V delay. If, during the V-A interval, no spontaneous atrial event is sensed, the pacer provides an atrial stimulus at the conclusion of the V-A interval.

In this type of pacemaker, in the absence of spontaneous P-waves and R-waves, the heart will be stimulated at fixed A—A and V—V intervals with a programmable AV delay. However, if the ventricle depolarizes spontaneously, then the A-V delay is truncated and the observed A—A interval is not fixed and will be shorter than the arithmetic sum of the programmed A-V and V-A intervals.

The dual chamber modalities, DVI, VAT, VDD and DDD, have proven to be especially efficacious pacemakers since they restore A-V synchrony and thus improve cardiac output by ensuring the hemodynamic contribution of the atrial chambers within the pacing regimen. The latter three modes also synchronize the pacing rate to the patient's native atrial or sinus rate and thus provide an increased pacing rate in response to bodily activity. Increasing cardiac rate is the major contributor to increased cardiac output. More recently, other pacers, which increase cardiac output in response to exercise, have been proposed. They include pacemakers that rely upon the sensing of physical via an activity sensor or accelerometer, changes in blood pH, respiratory rate, or QT interval. These data are used to alter the pacemaker's escape interval.

One approach that is important to the understanding of the present invention is the activity responsive pacer described in U.S. Pat. No. 4,428,378, issued to Anderson et al, and which is incorporated by reference. The pacer disclosed in that patent monitors the physical activity of the patient and increases the pacing rate in response to increasing patient activity.

Other publications that provide background information for the operation of the present invention include U.S. Pat. No. 4,890,617 issued to Markowitz et al. that is incorporated herein by reference. This patent describes a dual chamber activity responsive pacemaker that senses and paces in both the atrium and the ventricle. The pacing rate is determined by the sensed activity of the patient, the programmed lower rate, and the patient's atrial or sinus rate.

U.S. Pat. No. 4,932,046, entitled "Dual Chamber Rate Responsive Pacemaker", assigned to Medtronic, Inc. of Minneapolis, Minn., which is incorporated herein by reference, describes a dual chamber rate responsive pacemaker. The pacemaker operates in an atrial-synchronized modality when the sensed atrial rate is present, and paces at the sensor-determined rate when the sensed atrial rate is absent or below the programmed lower rate.

The above pacing modes may, in a certain sense, be considered as subsets to the DDD/R mode though, in reality, they were all developed from the VVI mode in one way or another. All such possibilities have been described in The NBG Code, a five-position code, published and updated as a joint effort of the North American Society of Pace and Electrophysiology (NASPE) and the British Pacing and Electrophysiology Group (BPEG). This code is generally used by those familiar with the state of the art and may be found in publications too numerous to mention.

DDD pacemakers are often implanted in patients with Sick Sinus Syndrome (SSS), a term that covers a large array of sinus node disease states. Such patients often have intact AV conduction and, if the pacemaker's AV interval is not properly programmed, the pacemaker will deliver an unneeded and undesirable ventricular pacing pulse. Many patients who receive DDD pacers or dual-chamber PCD (Pacer/Cardioverter/Defibrillator) devices are unnecessarily paced in the ventricle. There appears to be reluctance in the medical community against implanting a DDD device and programming it to the AAI/R mode in patients with sick sinus syndrome (SSS) and intact AV conduction. Moreover, when programmed to the DDD mode, the AV intervals in these pacemakers may be left at their factory-programmed state, that is, with shorter durations more suitable to third degree AV block patients. Or, even when programmed to a slightly longer duration, the A-V duration may become a compromise between a duration that promotes ventricular conduction and one which allows ventricular tracking up to high rates. As a result, ventricular pacing occurs at the termination of these intervals, with little or no possibility of spontaneous ventricular activity being allowed.

There is growing medical evidence that inappropriate ventricular pacing has disadvantageous short-term hemodynamic effects and may prove harmful when allowed to continue for an extended period of time. It has been know in the art as early as 1925 that ventricular pacing results in asynchronous delayed activation of the ventricular tissue and, thereby, produces compromised hemodynamics in mammals. More recently, canine studies have shown that right ventricular apical (RVA) pacing causes a negative inotropic effect and a >30% reduction in cardiac efficiency. In addition, long term RVA pacing has been shown to lead to permanent changes including myofibrillar cellular disarray, myocardial perfusion defects, and structural abnormalities. Each of these may further contribute to deterioration of left ventricular function.

The various manufacturers, including Medtronic, Inc., have attempted to address this problem by implementing algorithms that automatically adapt the AV interval duration to preferentially allow AV conduction when present.

In the U.S. Pat. No. 5,861,007, issued to Hess, et al, a Search AV operation is described in which the pacemaker continuously monitors for the presence or absence of an intrinsic R-wave after both sensed and paced P-waves. The programmed AV interval may be extended by a programmable "hysteresis" interval to promote ventricular conduction. The AV interval, however, cannot exceed 350 milliseconds in duration. To maintain unimpeded upper rate operation, Search AV works in conjunction with Auto-PVARP to maintain atrial sensing and tracking up to the programmed upper rate, thereby postponing a 2:1 block operation as long as possible. Since there is a limit to the shortening of the PVARP in this operation, it becomes necessary to shorten the AV interval after the PVARP reaches its maximum decrementation. Consequently, many patients (>30%) with intact AV conduction are ventricularly paced to a significant degree (>50%) in spite of having Search AV programmed on.

Another approach to the problem is presented in U.S. Pat. No. 5,318,594 issued to Limousin, et al. The DDD Automatic Mode Switch (AMS) mode operates in a "Special AAI" mode as long as R-wave sensing occurs within a ventricular surveillance window that is calculated based on the history of the measured PR interval. If an R-wave is not sensed within this window, the pacing operation switches to the DDD mode. After 100 consecutive paced ventricular events, the pacemaker attempts to switch back to the Special AAI mode. Although this operation has been shown to reduce ventricular pacing, because of operational restrictions, it has been only partially effective. A recent study of patients with predominantly intact AV conduction demonstrates ventricular pacing reduction from a mean of ~65% to ~36%.

A third approach presented in U.S. Pat. No. 6,122,546 issued to Sholder et al implements a form of AV/PV hysteresis. This operation encourages intrinsic conduction by extending the AV interval by a predetermined period beyond the programmed duration. As indicated above, this operation is restricted to avoid interaction with upper rate tracking. There is nothing in the literature to indicate one way or the other if it provides a true benefit to the patient. One can assume, however, that the reduction in ventricular pacing will be approximately that which has already been cited above.

Although present in bradycardia pacemakers, AV extension algorithms have been absent in dual chamber (DC) cardioverter defibrillators (ICDs). AV extension presents a unique challenge in DC ICDs due to the added requirements of tachyarrhythmia detection. For example, to adequately detect a ventricular tachycardia, the AV delay must be restricted so that the tachy detection interval (TDI) falls within the VA interval at all times. Failure to do so comes at the expense of tachyarrhythmia detection sensitivity. An alternative means to address this issue is by means of a temporary mode change for a programmed period of time following the delivery of a shock. Unfortunately, while this may protect against transient post-shock AV block, it does so at the expense of beat-to-beat monitoring. Consequently, many electrophysiologists do not program the AAI/R mode on a permanent basis to avoid persistent ventricular pacing. "Ideoventricular kick," first described by Schlant in 1966, (*Circulation,* 1966; 23 & 24 (Suppl. III): 209) results from improved coherence of the ventricular contraction during normal activation. This hemodynamic benefit is lost during ventricular pacing. In an earlier study of the atrial contribution to ventricular filling (Kosowski B, et al. Re-evaluation of the atrial contribution to ventricular filling: Study showing his-bundle pacing. *Am J Cardiol,* 1968; 21 518–24), it was demonstrated that ventricular function was better during normal ventricular activation independent of the PR interval. Similarly, a later study (Rosenqvist M, et al. Relative importance of activation sequence compared to atrioventricular filling synchrony in left ventricular function. *Am J Cardiol,* 1991; 67(2): 148–56) showed that AAI pacing was superior to either VVI or DDD pacing.

Aside from the hemodynamic benefits mentioned above, it may be that normal ventricular activation has a role in preventing tachyarrhythmias. In a study of 77 ICD patients with a mean follow-up of 18.7 months (Roelke M, et al. Ventricular pacing induced ventricular tachycardia in patients with implantable cardioverter defibrillators. *PACE,* 1995; 18(3): 486–91), appropriately timed ventricular pacing preceded tachyarrhythmia onset in 8.3% of the episodes in five patients. A further study (Belk P, et al. Does ventricular pacing predispose to ventricular tachycardia? Abstract. *PACE,* April, 2000) demonstrates that high rate ventricular pacing renders patients more susceptible to the induction of ventricular tachycardia compared to high rate atrial pacing with normal ventricular activation.

These studies, combined with the growing body of evidence showing the detrimental effects of long-term ventricular pacing, has led to more deliberate efforts by clinicians to allow for normal ventricular activation when programming dual chamber bradycardia devices. Still, due to the interactions imposed by PVARP and upper rate timing, mode switching, and tachyarrhythmia detection, their best intentions are often thwarted. The present invention, however, goes a long way toward answering all the issues posed by previous patents, as well as those in the published literature.

SUMMARY OF THE INVENTION

The present invention encompasses a novel mode of a pacing called the Preferred ADI/R mode. This mode is intended to be an ON/OFF selection that operates as a subset of the programmed DDD/R mode. Although this mode is framed in the standard NBG nomenclature, it is does not use the "bottom-up" approach (that is, stemming from the VVI mode), but rather the "top-down" approach (that is, deriving from an A-V perspective). This mode is primarily indicated for use with SSS patients who constitute some 66% of all patients who received a pacemaker. Some of these patients have concomitant third degree AV block. There remains, however, a significant majority who either have intact AV conduction, or AV block in which AV conduction is present in varying degrees (that is, first degree or second degree Mobitz type I).

When programmed to the ADI/R mode, the pacemaker checks on a beat-to-beat basis for intact AV conduction. The pacemaker will continue to pace the atrium and allow the conducted ventricular event to take place. If, however, intermittent AV block does occur, the mode automatically switches to the DDI/R or DDD/R mode for one, or as many cycles as necessary, and upon the detection of the presence of AV conduction, the mode switches back to the ADIR/R mode.

The preferred ADI/R mode operates preferentially as it continually monitors the ventricular response. This mode may be used in those patients with intact AV conduction or intermittent AV block. The purpose of this mode is to ensure AV conduction whenever possible so as to gain all the benefits from the contractile properties accruing from native R-waves. In those instances where the AV conduction system is intermittently blocked (such as might occur in a rate-induced block), the pacing mode is automatically switched to a committed DDI/R mode with a short AV delay to ensure a paced R-wave. The cycle that follows is in the DDD/R mode with a longer AV delay to determine if conduction has returned. If so, ADIR pacing resumes with continued monitoring for intrinsic AV conduction.

The present invention, that is, the permanent pacing mode, Preferred ADI/R, is indicated for patients with sick sinus syndrome, with intact AV conduction, first degree or second degree (Mobitz II) block. This mode is superior to permanent DDD/R, especially in ICD patients. This mode allows for greater programming flexibility and fewer interactions with other programmable parameters. Intrinsic conduction and normal ventricular activation/contraction is promoted by this mode with all of its attendant benefits. In addition the DDD/R mode is available as a backup mode providing a safety net for those times when a patient unexpectedly experiences intermittent high grade AV block.

DETAILED DESCRIPTION OF THE DRAWINGS

Figure 1:
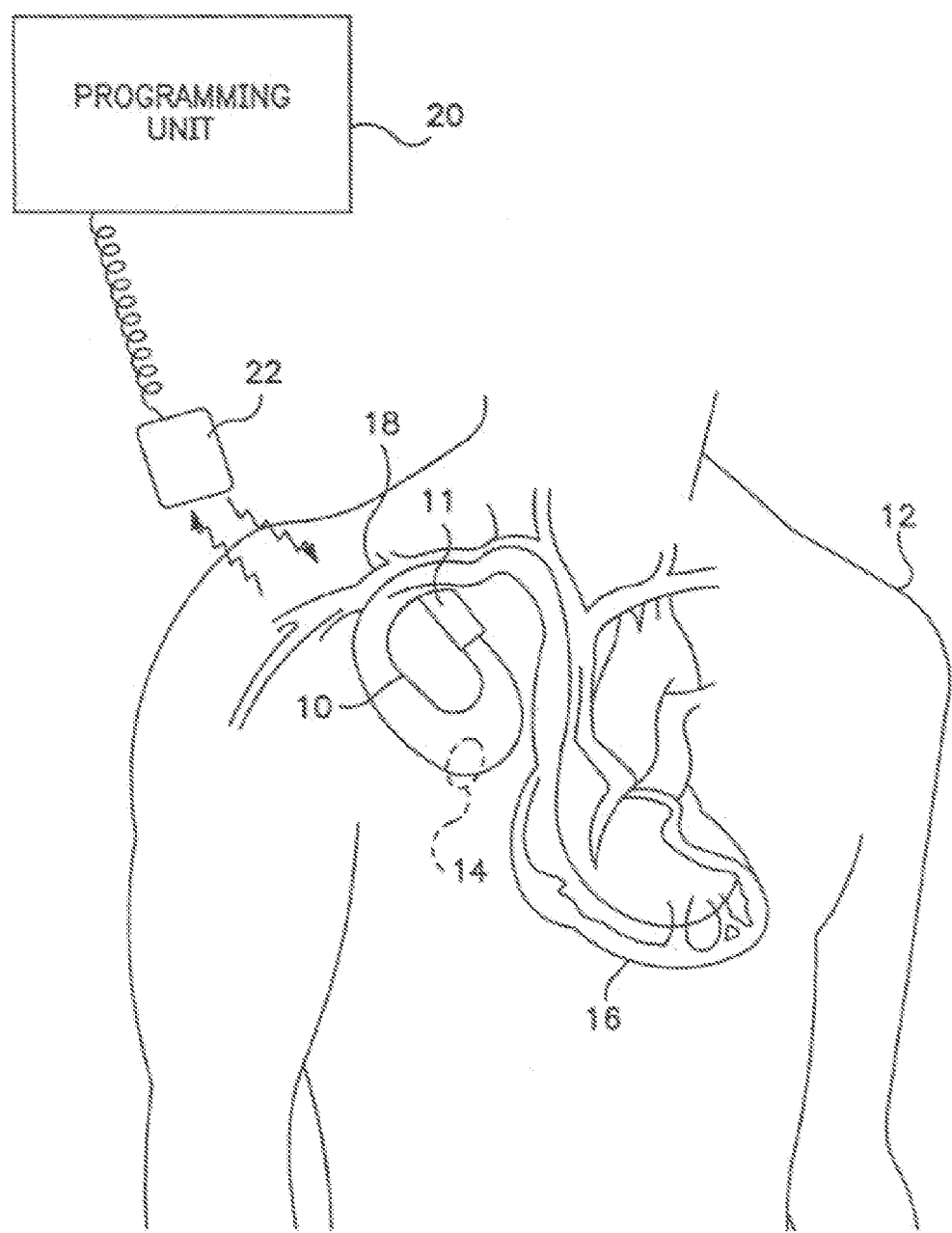
FIG. 1 is an illustration of a body-implantable device system in accordance with the present invention, including a hermetically sealed device implanted in a patient and an external programming unit.

FIG. 1 is an illustration of an implantable medical device system adapted for use in accordance with the present invention. The medical device system shown in FIG. 1 includes an implantable device 10—a pacemaker in this embodiment—that has been implanted in a patient 12. In accordance with conventional practice in the art, pacemaker 10 is housed within a hermetically sealed, biologically inert outer casing, which may itself be conductive so as to serve as an indifferent electrode in the pacemaker's pacing/sensing circuit. One or more pacemaker leads, collectively identified with reference numeral 14 in FIG. 1 are electrically coupled to pacemaker 10 in a conventional manner and extend into the patient's heart 16 via a vein 18. Disposed generally near the distal end of leads 14 are one or more exposed conductive electrodes for receiving electrical cardiac signals and/or for delivering electrical pacing stimuli to heart 16. As will be appreciated by those of ordinary skill in the art, leads 14 may be implanted with its distal end situated in the atrium and/or ventricle of heart 16.

Although the present invention will be described herein in one embodiment which includes a pacemaker, those of ordinary skill in the art having the benefit of the present disclosure will appreciate that the present invention may be advantageously practiced in connection with numerous other types of implantable medical device systems, and indeed in any application in which it is desirable to provide the preferred ADI/R pacing mode, as may occur in ICDs.

Also depicted in FIG. 1 is an external programming unit 20 for non-invasive communication with implanted device 10 via uplink and downlink communication channels, to be hereinafter described in further detail. Associated with programming unit 20 is a programming head 22, in accordance with conventional medical device programming systems, for facilitating two-way communication between implanted device 10 and programmer 20. In many known implantable device systems, a programming head such as that depicted in FIG. 1 is positioned on the patient's body over the implant site of the device (usually within 2- to 3-inches of skin contact), such that one or more antennae within the head can send RF signals to, and receive RF signals from, an antenna disposed within the hermetic enclosure of the implanted device or disposed within the connector block of the device, in accordance with common practice in the art.

Figure 2:
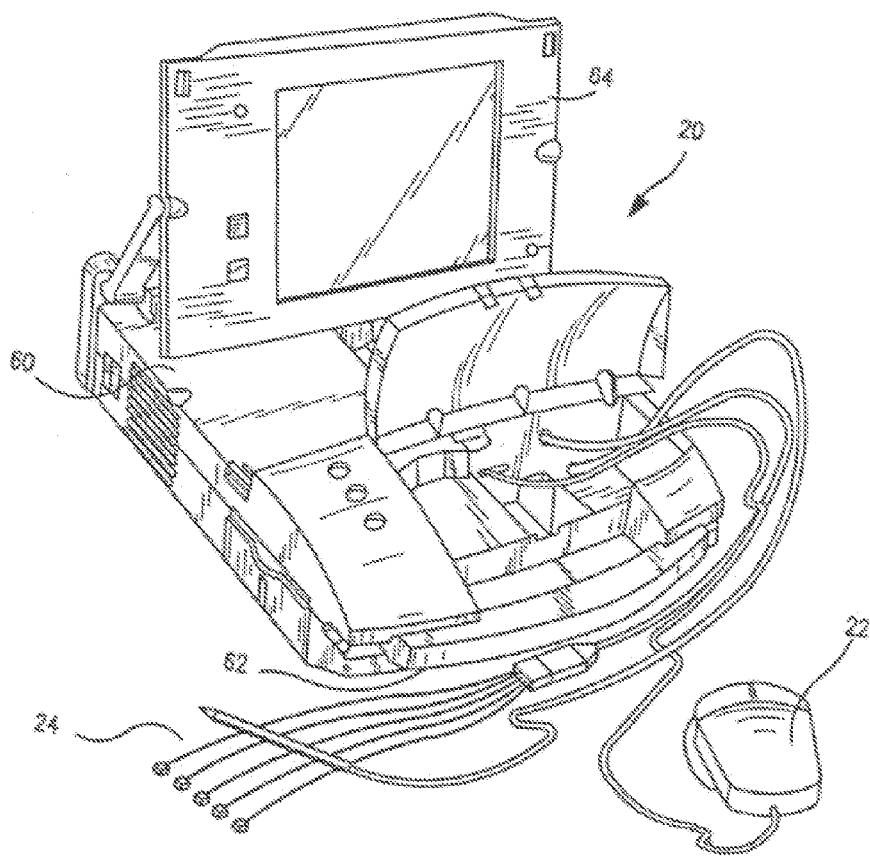
FIG. 2 is a perspective view of the external programming unit of FIG. 1.

FIG. 2 is a perspective view of programming unit 20 in accordance with the presently disclosed invention. Internally, programmer 20 includes a processing unit (not shown in the Figure) that in accordance with the presently disclosed invention is a personal computer type motherboard, e.g., a computer motherboard including an Intel Pentium 3 microprocessor and related circuitry such as digital memory. The details of design and operation of the programmer's computer system will not be set forth in detail in the present disclosure, as it is believed that such details are well-known to those of ordinary skill in the art.

Referring to FIG. 2, programmer 20 comprises an outer housing 60, which is preferably made of thermal plastic or another suitably rugged yet relatively lightweight material. A carrying handle, designated generally as 62 in FIG. 2, is integrally formed into the front of housing 60. With handle 62, programmer 20 can be carried like a briefcase.

An articulating display screen 64 is disposed on the upper surface of housing 60. Display screen 64 folds down into a closed position (not shown) when programmer 20 is not in use, thereby reducing the size of programmer 20 and protecting the display surface of display 64 during transportation and storage thereof.

A floppy disk drive is disposed within housing 60 and is accessible via a disk insertion slot (not shown). A hard disk drive is also disposed within housing 60, and it is contemplated that a hard disk drive activity indicator, (e.g., an LED, not shown) could be provided to give a visible indication of hard disk activation.

As would be appreciated by those of ordinary skill in the art, it is often desirable to provide a means for determining the status of the patient's conduction system. To accomplish this task and provide suitable ECG tracings, programmer 20 is equipped with external ECG leads 24.

In accordance with the present invention, programmer 20 is equipped with an internal printer (not shown) so that a hard copy of a patient's ECG or of graphics displayed on the programmer's display screen 64 can be generated. Several types of printers, such as the AR-100 printer available from General Scanning Co., are known and commercially available.

In the perspective view of FIG. 2, programmer 20 is shown with articulating display screen 64 having been lifted up into one of a plurality of possible open positions such that the display area thereof is visible to a user situated in front of programmer 20. Articulating display screen is preferably of the LCD or electro-luminescent type, characterized by being relatively thin as compared, for example, a cathode ray tube (CRT) or the like.

As would be appreciated by those of ordinary skill in the art, display screen 64 is operatively coupled to the computer circuitry disposed within housing 60 and is adapted to provide a visual display of graphics and/or data under control of the internal computer.

Programmer 20 described herein with reference to FIG. 2 is described in more detail in U.S. Pat. No. 5,345,362 issued to Thomas J. Winkler, entitled "Portable Computer Apparatus With Articulating Display Panel," which patent is hereby incorporated herein by reference in its entirety. The Medtronic Model 9790 programmer is the implantable device-programming unit with which the present invention may be advantageously practiced.

Figure 3:
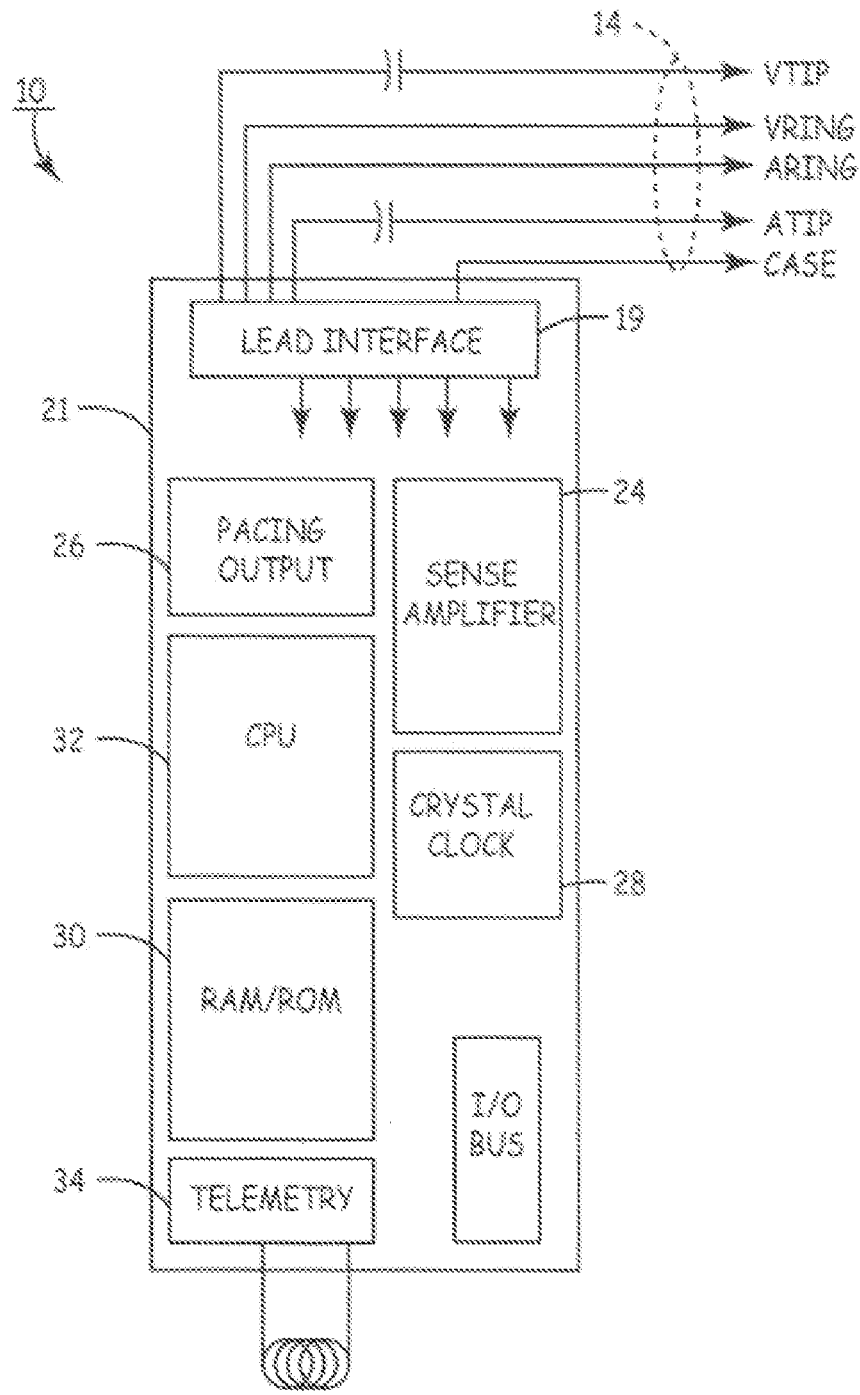
FIG. 3 is a block diagram of the implanted device from FIG. 1.

FIG. 3 is a block diagram of the electronic circuitry that makes up pulse generator 10 in accordance with the presently disclosed invention. As can be seen from FIG. 3, pacemaker 10 comprises a primary stimulation control circuit 20 for controlling the device's pacing and sensing functions. The circuitry associated with stimulation control circuit 21 may be of conventional design, in accordance, for example, with what is disclosed U.S. Pat. No. 5,052,388 issued to Sivula et al., "Method and apparatus for implementing activity sensing in a pulse generator." To the extent that certain components of pulse generator 10 are conventional in their design and operation, such components will not be described herein in detail, as it is believed that design and implementation of such components would be a matter of routine to those of ordinary skill in the art. For example, stimulation control circuit 21 in FIG. 3 includes sense amplifier circuitry 24, stimulating pulse output circuitry 26, a crystal clock 28, a random-access memory and read-only memory (RAM/ROM) unit 30, and a central processing unit (CPU) 32, all of which are well-known in the art.

Pacemaker 10 also includes internal communication circuit 34 so that it is capable communicating with external programmer/control unit 20, as described in FIG. 2 in greater detail.

With continued reference to FIG. 3, pulse generator 10 is coupled to one or more leads 14 which, when implanted, extend transvenously between the implant site of pulse generator 10 and the patient's heart 16, as previously noted with reference to FIG. 1. Physically, the connections between leads 14 and the various internal components of pulse generator 10 are facilitated by means of a conventional connector block assembly 11, shown in FIG. 1. Electrically, the coupling of the conductors of leads and internal electrical components of pulse generator 10 may be facilitated by means of a lead interface circuit 19 which functions, in a multiplexer-like manner, to selectively and dynamically establish necessary connections between various conductors in leads 14, including, for example, atrial tip and ring electrode conductors ATIP and ARING and ventricular tip and ring electrode conductors VTIP and VRING, and individual electrical components of pulse generator 10, as would be familiar to those of ordinary skill in the art. For the sake of clarity, the specific connections between leads 14 and the various components of pulse generator 10 are not shown in FIG. 3, although it will be clear to those of ordinary skill in the art that, for example, leads 14 will necessarily be coupled, either directly or indirectly, to sense amplifier circuitry 24 and stimulating pulse output circuit 26, in accordance with common practice, such that cardiac electrical signals may be conveyed to sensing circuitry 24, and such that stimulating pulses may be delivered to cardiac tissue, via leads 14. Also not shown in FIG. 3 is the protection circuitry commonly included in implanted devices to protect, for example, the sensing circuitry of the device from high voltage stimulating pulses.

As previously noted, stimulation control circuit 21 includes central processing unit 32 which may be an off-the-shelf programmable microprocessor or micro controller, but in the present invention is a custom integrated circuit. Although specific connections between CPU 32 and other components of stimulation control circuit 21 are not shown in FIG. 3, it will be apparent to those of ordinary skill in the art that CPU 32 functions to control the timed operation of stimulating pulse output circuit 26 and sense amplifier circuit 24 under control of programming stored in RAM/ROM unit 30. It is believed that those of ordinary skill in the art will be familiar with such an operative arrangement.

With continued reference to FIG. 3, crystal oscillator circuit 28, in the presently preferred embodiment a 32,768-Hz crystal controlled oscillator provides main timing clock signals to stimulation control circuit 20. Again, the lines over which such clocking signals are provided to the various timed components of pulse generator 10 (e.g., microprocessor 32) are omitted from FIG. 3 for the sake of clarity.

It is to be understood that the various components of pulse generator 10 depicted in FIG. 3 are powered by means of a battery (not shown) that is contained within the hermetic enclosure of pacemaker 10, in accordance with common practice in the art. For the sake of clarity in the Figures, the battery and the connections between it and the other components of pulse generator 10 are not shown.

Stimulating pulse output circuit 26, which functions to generate cardiac stimuli under control of signals issued by CPU 32, may be, for example, of the type disclosed in U.S. Pat. No. 4,476,868 to Thompson, entitled "Body Stimulator Output Circuit," which patent is hereby incorporated by reference herein in its entirety. Again, however, it is believed that those of ordinary skill in the art could select from among many various types of prior art pacing output circuits that would be suitable for the purposes of practicing the present invention.

Sense amplifier circuit 24, which is of conventional design, functions to receive electrical cardiac signals from leads 14 and to process such signals to derive event signals reflecting the occurrence of specific cardiac electrical events, including atrial contractions (P-waves) and ventricular contractions (R-waves). CPU provides these event-indicating signals to CPU 32 for use in controlling the synchronous stimulating operations of pulse generator 10 in accordance with common practice in the art. In addition, these event-indicating signals may be communicated, via uplink transmission, to external programming unit 20 for visual display to a physician or clinician.

Those of ordinary skill in the art will appreciate that pacemaker 10 may include numerous other components and subsystems, for example, activity sensors and associated circuitry. The presence or absence of such additional components in pacemaker 10, however, is not believed to be pertinent to the present invention, which relates primarily to the implementation and operation of communication subsystem 34 in pacemaker 10, and an associated communication subsystem in external unit 20.

Figure 4:
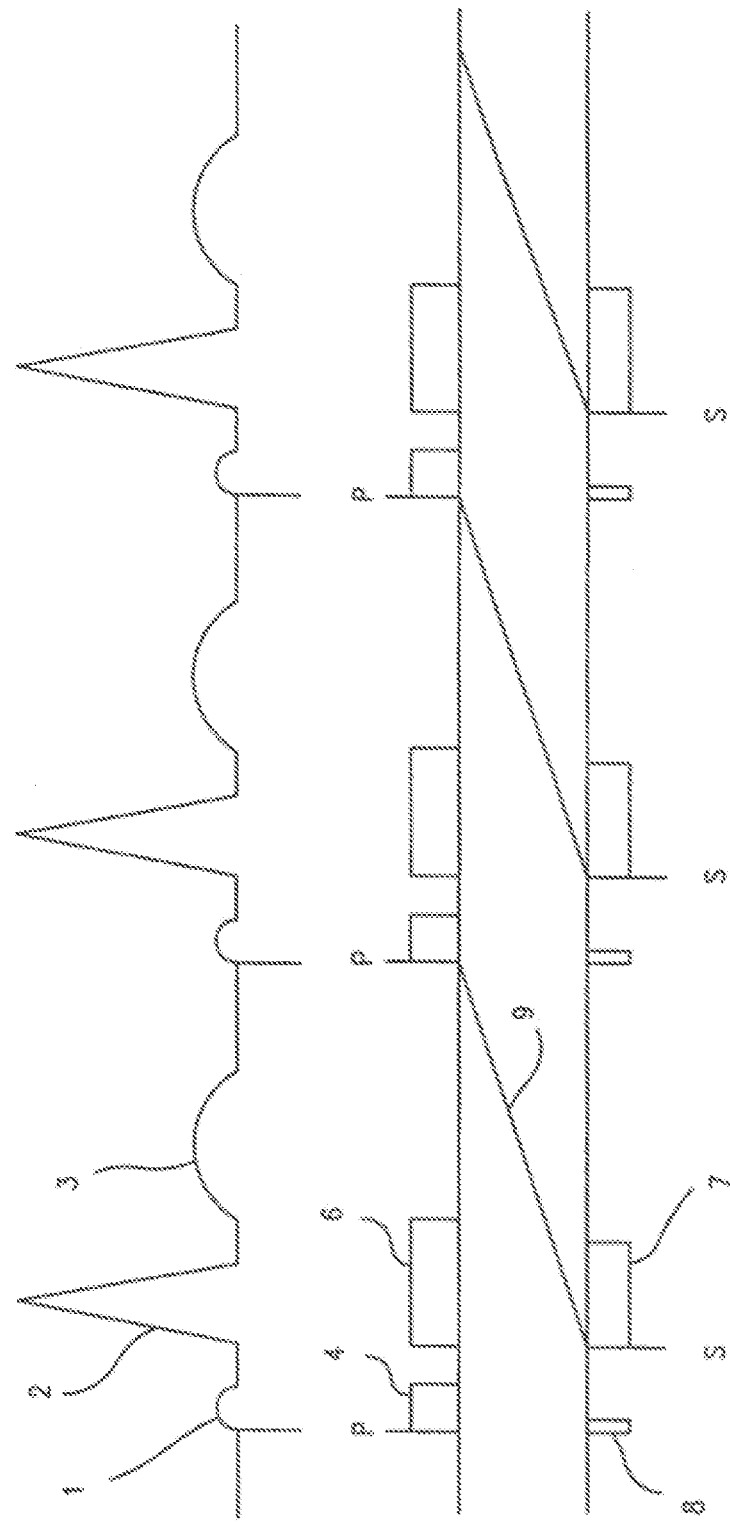
FIG. 4 is a ladder diagram of the ADI/R operation.

FIG. 4 is a ladder diagram of the ADI/R operation, specifically a Marker Channel® Diagram. With the help of the NBG Code, one familiar with the state of the art will be able to discern that the letter in the first position (A) means that the pacemaker (or other implanted device) will pace the atrium in the absence of an atrial sensed event. The second letter (D) implies that the pacemaker will sense in dual chambers, that is, both the atrial and ventricular chambers. The third letter (I) means that, upon sensing in either chamber, pacing will be inhibited in that specific chamber. The final letter, R, implies that the device may be rate responsive, that is, altering the atrial rate in response to an artificial sensor, such as a Piezo-electrical crystal, accelerometer, minute ventilation, etc.

The operation of the preferred ADI/R mode is depicted in the ladder diagram as follows. Atrial paced (or sensed) event 1 initiates a non-programmable, auto-adjusting (e.g., 100–150 millisecond) blanking period 4, followed by auto-adjusting atrial sensitivity (not shown). Sensing circuitry (see FIG. 3) determines if and when ventricular sensed event 2 has occurred. If detected, timing circuitry (see FIG. 3) initiates VA interval 9. Other timing, blanking periods, and refractory periods serve the following purposes. A programmable ventricular blanking period 8 prevents sensing of atrial pace 1 on the ventricular channel, sometimes termed "crosstalk." Ventricular sensed event 2 starts a 120 millisecond post ventricular atrial blanking (PVAB) period 6, followed by auto-adjusting atrial sensitivity. PVAB 6 serves the purpose of preventing sensing of the R-wave or T-wave on the atrial channel, termed "far-field R-wave sensing." Ventricular sensed event 2 also starts 100 millisecond ventricular blanking 7 followed by auto-adjusting ventricular sensitivity. This period serves the purpose of preventing sensing of the ventricular output pulse or the ventricular depolarization itself. Repolarization, or T-wave 3, follows R-wave 2. Ventricular event 2 detected by sensing circuitry (see FIG. 3) sends signal to timing circuitry to start VA interval 9, leading to the next atrial pacing cycle.

Figure 5:
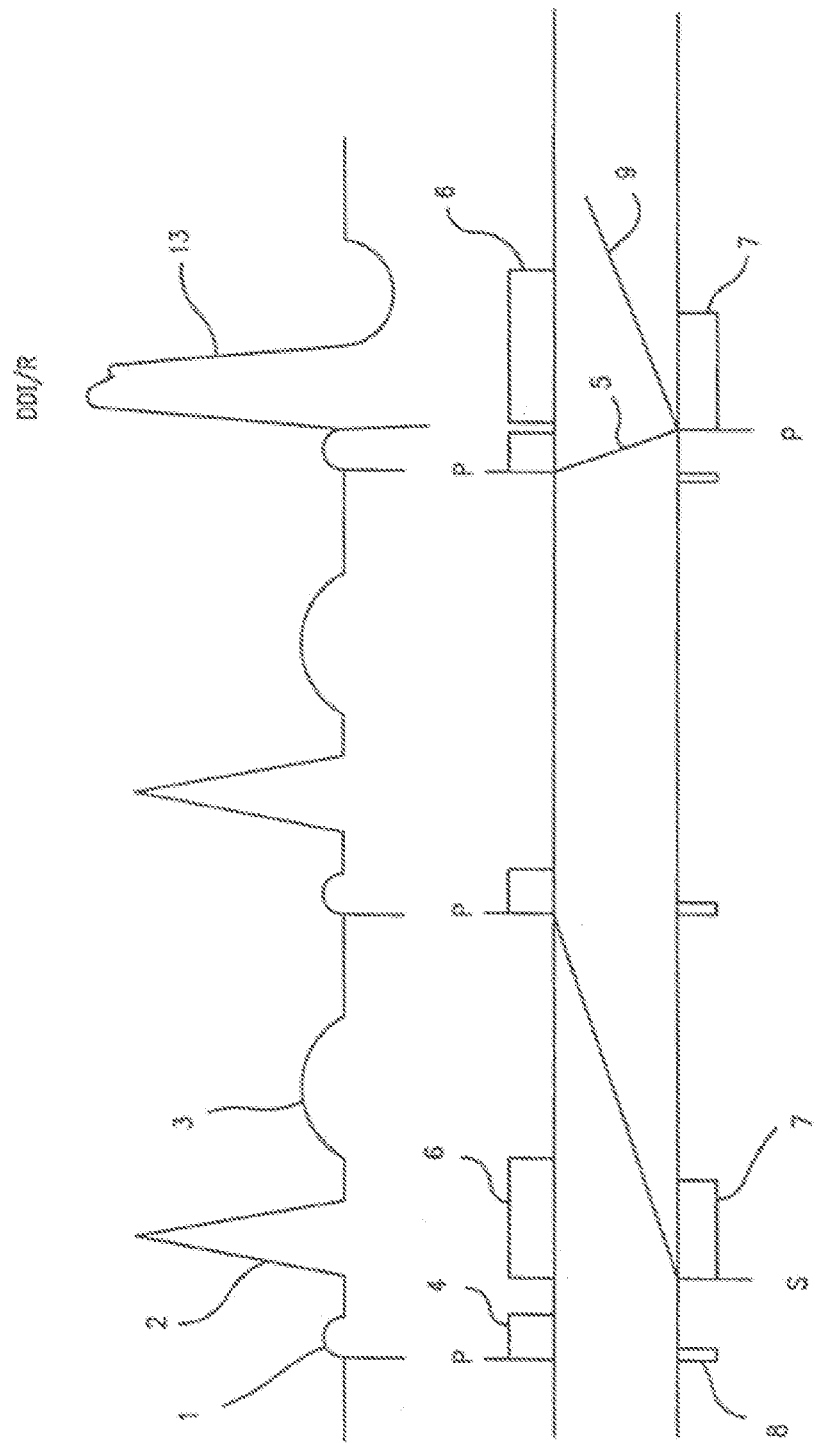
FIG. 5 is a ladder diagram of the committed DDD/R operation in the event that the patient develops transient AV block.

Taking into account that this mode would be used primarily with Sick Sinus patients who have full or some degree of intact AV conduction, this type of operation as depicted for the ADI/R mode is something the clinician or physician would expect to occur. In the presence of intact AV conduction, even if it is prolonged, the pacemaker will maintain the ADI/R operation/mode. Sensed ventricular events would occur in the vast majority of cardiac cycles (that is, PQRST). FIG. 5 teaches what will occur should the patient develop transient AV block for one or a few cardiac cycles.

FIG. 5 is a ladder diagram of the committed DDI/R operation in the event that the patient develops transient AV block. The purpose of the committed DDI/R operation is to maintain ventricular support in the presence of AV block. Briefly stated, the implanted device mode switches from the preferred ADI/R to the committed DDI/R for one cycle.

The timing of the Committed DDI/R is as follows. In the DDI/R mode (third pacing cycle, labeled DDI/R), AV interval 5 is set to a short 80 milliseconds, following the Paced P-wave due to the absence of any sensed ventricular event between the second and third atrial paced events. The purpose of this short AV interval 5 is to suppress competition between ventricular pacing pulse culminating in paced R-wave 13 and any potential intrinsic R-wave with a delayed conduction from the previous paced atrial event.

Assuming the presence of such an intrinsic R-wave, the timing of the ventricular output pulse would normally result in a ventricular pacing pulse falling into the absolute refractory period of the intrinsic, conducted R-wave, resulting in a psuedo-fusion beat (not shown). This operation is intended to prevent the onset of a ventricular tachycardia, should the ventricular pacing pulse fall into the relative refractory period of the ventricle, commonly called "pacing on T" phenomenon.

Continuing with the timing in FIG. 5, paced R-wave 13 starts a 120 millisecond ventricular blanking period 7, followed by auto adjusting ventricular sensitivity (not shown). Paced R-wave 13 also starts a 120 millisecond PVAB 6 followed by auto adjusting atrial sensitivity (not shown). Assuming the transient AV block self-corrects and a sensed R-wave is detected, the preferred ADI/R resumes with the next paced or sensed P-wave, as is depicted in FIG. 4.

Figure 6:
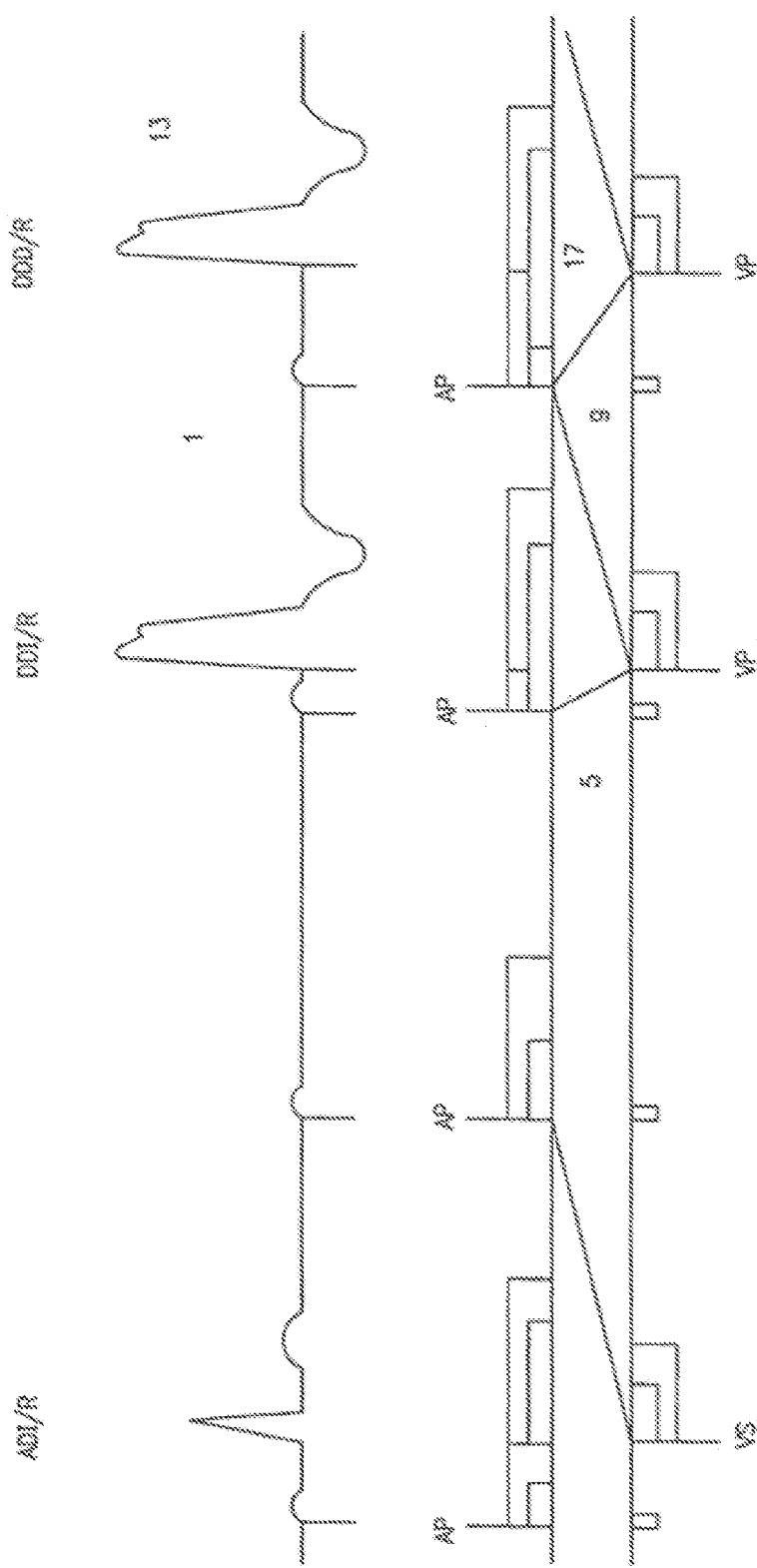
FIG. 6 is a ladder diagram that depicts the pacing operation in the event that the patient develops AV block that persists for more than one cycle.
Figure 7:
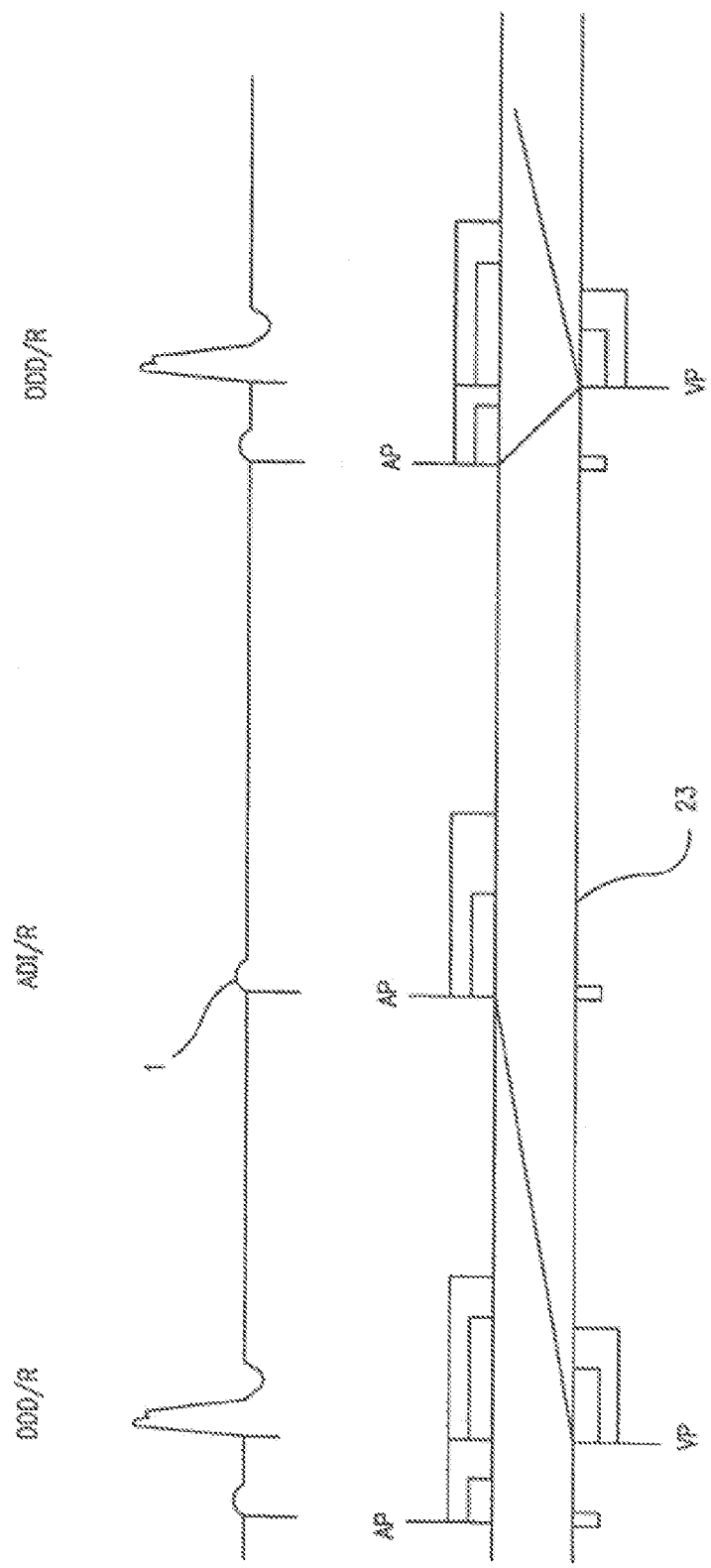
FIG. 7 is a ladder diagram that depicts a periodic attempt to restore the ADI/R operation during sustained DDD/R operation.

FIG. 6 is a ladder diagram that depicts the pacing operation in the event that the patient develops AV block that persists for more than one cycle. This figure is a continuation of FIG. 5. Following the one-cycle mode switch to DDI/R, VA interval 9 times out, resulting in atrial paced event 1. A very long (e.g. 400 millisecond or up to 65% of the sensor-indicated AV interval) 17 is used in an attempt to promote AV conduction. If, however, AV interval 17 is not interrupted by a sensed, intrinsic R-wave, as is depicted in the first cycle (labeled ADI/R), the pacemaker immediately switches to the DDD/R mode. In the event that a sensed, intrinsic R-wave does occur, the device would revert to the ADI/R operation (not shown). The DDD/R operation, with the programmed AV interval, will be sustained until a sensed, intrinsic R-wave is detected, as is shown in FIG. 7. Periodic attempts to force restoration of the ADI/R operation are performed (as depicted in FIG. 7). Mode switching to the DDI/R mode will occur in the event that an atrial tachycardia is detected (see FIG. 8).

FIG. 7 is a ladder diagram that depicts a periodic attempt to restore the ADI/R operation during sustained DDD/R operation. As mentioned, the DDD/R mode may become the sustained mode of operation in the event that the patient develops a prolonged AV block, such as might occur with rate-dependent AV block. In such cases, the device may be programmed to revert to ADI/R 1 after a programmable number of DDD/R cycles. Then, the device looks for a ventricular sensed event, e.g., at 23 following atrial pace 1. In the event that a sensed, intrinsic R-wave is detected, the ADI/R operation is immediately resumed. In the absence of a ventricular sensed event, the device continues to operate in the DDD/R mode, as indicated in the third cycle of FIG. 7.

Figure 8:
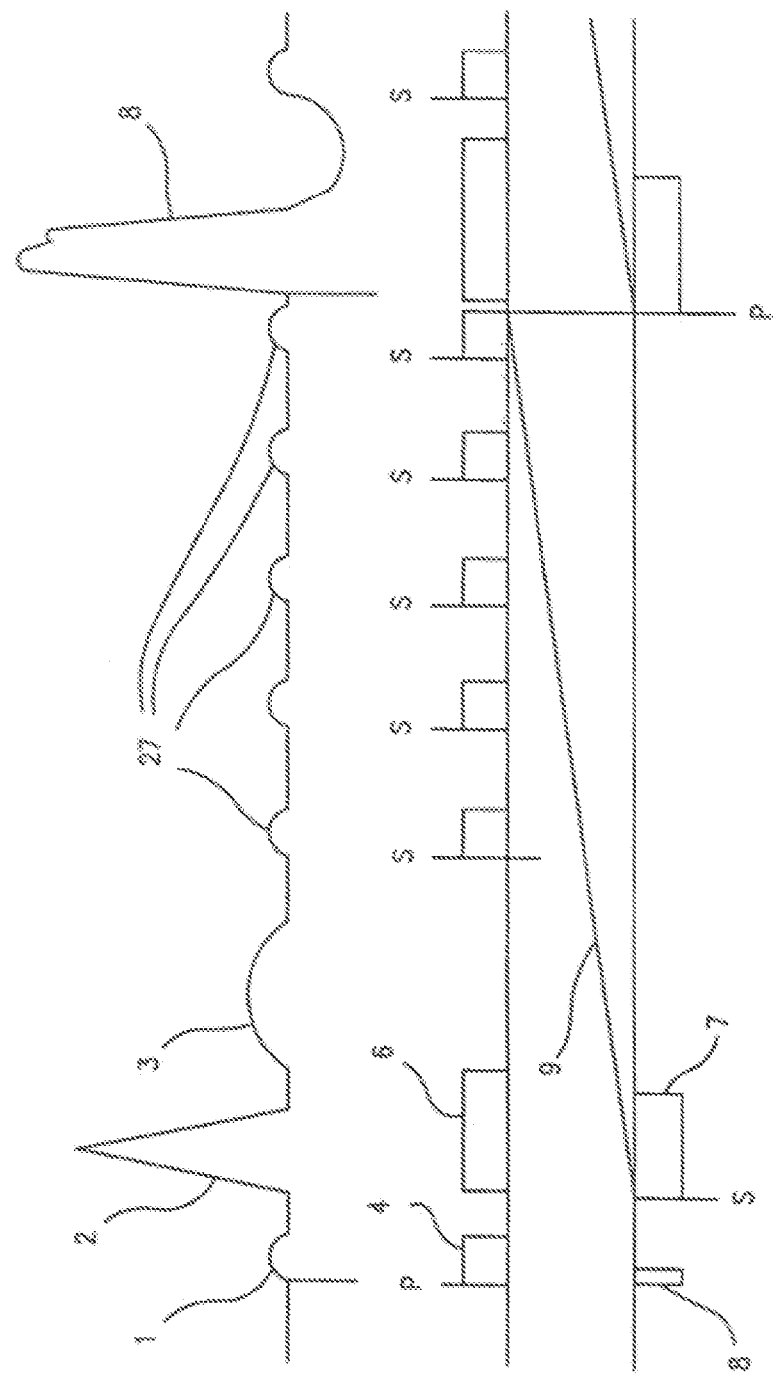
FIG. 8 is a ladder diagram of the pacing operation in the event that the patient develops an atrial tachycardia.

FIG. 8 is a ladder diagram of the pacing operation in the event that the patient develops an atrial tachycardia. A sick sinus patient often has episodes of atrial tachycardia, atrial flutter, or atrial fibrillation. During these episodes, the pacing operation must be such that the ventricular pacing rate will neither be synchronized to the fast atrial rate nor so slow as to cause symptoms.

In FIG. 5 it was noted that the device, while operating in the ADI/R mode, can switch to the DDI/R mode. The DDI/R mode is well suited for pacing in the presence of an atrial tachycardia because it will not allow ventricular synchronization to a fast atrial rate nor will it allow the ventricular pacing rate to go below the programmed lower rate. Therefore, when an atrial tachycardia does occur, as shown in FIG. 8, fast atrial sensed events 27 without a conducted ventricular event have no effect on ventricular timing 9. Since there is no ventricular event, the operation immediately switches to the DDI/R mode. In the presence of an atrial tachycardia, the V—V interval 9 times out so that paced R-wave 8 will occur at the faster of the programmed lower rate or sensor-indicated rate in the DDI/R mode. The operation depicted in FIG. 8 will continue so long as the atrial tachycardia persists. Upon termination of the atrial tachycardia, the preferred ADI/R will resume as shown in FIG. 4 or 7, depending on how the heart recovers from the atrial tachyarrhythmia. If the atrial tachyarrhythmia terminates abruptly, the prompt restoration of the ADI/R mode takes place (see FIG. 4). If, however, the atrial tachyarrhythmia "cools down" slowly, there may be a period of DDD/R pacing with periodic attempts to restore ADI/R pacing as shown in FIG. 7.

Since all patients may experience premature ventricular events (PVCs), the ADI/R operation treats the PVC as a sensed ventricular event that resets the VA interval. Such PVCs can occur during normal sinus rhythm or during an atrial tachyarrhythmia. In either case, the A—A timing is interrupted and reset by the PVC (not shown), an operation well known to those familiar with the state of the art. A PVC sensed during an atrial tachycardia inhibits the scheduled ventricular pacing pulse and resets the ventricular lower rate and sensor-indicated ventricular rate timers.

It is to be understood that the above description is intended to be illustrative and, not restrictive. Many other embodiments will be apparent to those of skill in the art upon reading and understanding the above description. The scope of the invention should, therefore, be determined with reference to the appended claims, along with the full scope of equivalents to which such claims are entitled.

The invention claimed is:

1. A method of selectively providing cardiac pacing with an implantable medical device (IMD) comprising:
   operating an IMD in an atrial based pacing mode;
   monitoring A—A intervals for ventricular activity;
   switching to a DDI pacing mode if no ventricular activity is sensed during a given A—A interval;
   delivering a ventricular support pacing pulse while in the DDI pacing mode;
   switching to a DDD pacing mode after delivering the ventricular support pacing pulse;
   determining if intact AV conduction is present, subsequent to switching to the DDD pacing mode; and
   switching to the atrial based pacing mode if intact AV conduction is present.

2. The method of claim 1, wherein the DDI pacing mode is in operation for no more than one consecutive cardiac cycle.

3. The method of claim 1, wherein switching to the DDI pacing mode includes switching to the DDI pacing mode for no more than one consecutive A—A interval.

4. The method of claim 1, wherein switching to the DDI pacing mode includes operating in the DDI pacing mode for an A—A interval immediately subsequent to the given A—A interval.

5. The method of claim 1, wherein switching to the DDI pacing mode includes switching to the DDI pacing mode upon termination of the given A—A interval.

6. The method of claim 1, wherein switching to the DDI pacing mode includes operating in the DDI pacing mode for at least a portion of an A—A interval immediately subsequent to the given A—A interval.

7. The method of claim 1, wherein determining if intact AV conduction is present includes varying at least one parameter of the DDD pacing mode.

8. The method of claim 1, wherein determining if intact AV conduction is present includes actively adjusting a pacing parameter.

9. The method of claim 1, wherein any delivered atrial pulse is at a level sufficient to achieve atrial capture.

10. The method of claim 1, wherein the atrial based pacing mode is selected from the group consisting of: AAI, AAI/R, ADI, ADI/R.

11. The method of claim 1, wherein the ventricular support pulse is delivered within an AV interval of about 80 milliseconds.

12. The method of claim 1, wherein determining if intact AV conduction is present includes determining if intact AV conduction is present during a first cycle operated in the DDD pacing mode.

13. The method of claim 12, wherein determining if intact AV conduction is present during the first cycle includes implementing an extended AV escape interval relative to normal DDD operation.

14. The method of claim 13, wherein sensed ventricular activity during the extended AV escape interval indicates intact AV conduction and triggers the switch to the atrial based pacing mode.

15. The method of claim 13, wherein cycles subsequent to the first cycle operated in the DDD pacing mode include implementing a normal AV escape interval that is shorter than the extended AV escape interval.

16. The method of claim 1, wherein determining if intact AV conduction is present while operating in the DDD pacing mode includes extending an AV escape interval for at least one cardiac cycle.

17. The method of claim 16, wherein extending the AV escape interval includes extending the AV escape interval to any length up to and including a length of an A—A interval.

18. The method of claim 17, wherein the DDD pacing mode will permit an A—A interval to transpire without ventricular activity while determining if intact AV conduction is present.

19. The method of claim 18, wherein only one A—A interval is permitted to transpire without ventricular activity while determining if intact AV conduction is present.

20. The method of claim 18, wherein multiple, non-sequential A—A intervals are permitted to transpire without ventricular activity during one session of checking for intact AV conduction.

21. The method of claim 16, wherein the DDD pacing mode will permit an A—A interval to transpire without ventricular activity while determining if intact AV conduction is present.

22. The method of claim 1, wherein determining if intact AV conduction is present includes inhibiting the delivery of a ventricular pace for one complete A—A interval.

23. The method of claim 1, wherein checking for intact AV conduction occurs periodically while in the DDD pacing mode.

24. The method of claim 1, wherein determining if intact AV conduction is present occurs during a first cycle operated in the DDD mode and inhibition of a ventricular pace is indicative of intact conduction.

25. An implantable medical device (IMD) for selectively providing cardiac pacing comprising:
   means for operating an IMD in an atrial based pacing mode;
   means for monitoring A—A intervals for ventricular activity;
   means for switching to a DDI pacing mode if no ventricular activity is sensed during a given A—A interval;
   means for delivering a ventricular support pacing pulse while in the DDI pacing mode;
   means for switching to a DDD pacing mode after delivering the ventricular support pacing pulse;
   means for determining if intact AV conduction is present, subsequent to switching to the DDD pacing mode; and
   means for switching to the atrial based pacing mode if intact AV conduction is present.

26. The IMD of claim 25, wherein the DDI pacing mode is in operation for no more than one consecutive cardiac cycle.

27. The IMD of claim 25, further comprising means for operating in the DDI pacing mode for no more than one consecutive A—A interval.

28. The IMD of claim 25, further comprising means for operating in the DDI pacing mode for an A—A interval immediately subsequent to the given A—A interval.

29. The IM of claim 25, wherein the means for switching to the DDI pacing mode further include means for switching to the DDI pacing mode upon termination of the given A—A interval.

30. The IMD of claim 25, further comprising means for operating in the DDI pacing mode for at least a portion of an A—A interval immediately subsequent to the given A—A interval.

31. The IMD of claim 25, wherein the means for determining if intact AV conduction is present include means for varying at least one parameter of the DDD pacing mode.

32. The IMD of claim 25, wherein the means for determining if intact AV conduction is present further include means for actively adjusting a pacing parameter.

33. The IMD of claim 25, wherein any atrial pulse delivered by the means for operating an IMD in the atrial based pacing mode during atrial based pacing is at a level sufficient to achieve atrial capture.

34. The IMD of claim 25, wherein the atrial based pacing mode is selected from the group consisting of: AAI, AAI/R, ADI, ADI/R.

35. The IMD of claim 25, wherein the ventricular support pulse is delivered within an AV interval of about 80 milliseconds.

36. The IMD of claim 25, wherein the means for determining if intact AV conduction is present determine if AV conduction is present during a first cycle operated in the DDD pacing mode.

37. The IMD of claim 36, wherein means for determining if intact AV conduction is present implement an extended AV escape during the first cycle operated in the DDD mode, wherein the extended AV escape interval is extended relative to a normal AV escape interval used in normal DDD operation.

38. The IMD of claim 37, wherein ventricular activity sensed during the extended AV escape interval indicates intact AV conduction and triggers the means for switching to the atrial based pacing mode.

39. The IMD of claim 37, further comprising means for operating in the DDD pacing mode that implement the normal AV escape interval for cycles subsequent to the first cycle operated in the DDD pacing mode.

40. The IMD of claim 25, wherein the means for determining if intact AV conduction is present while operating in the DDD pacing mode include means for extending an AV escape interval for at least one cardiac cycle.

41. The IMD of claim 40, wherein the means for extending the AV escape interval selectively extend the AV escape interval to any length up to and including a length of an A—A interval.

42. The IMD of claim 41, wherein the means for determining if intact AV conduction is present will permit an A—A interval to transpire without ventricular activity while operating in the DDD pacing mode.

43. The IMD of claim 42, wherein the means for determining if intact AV conduction is present will only permit one A—A interval to transpire without ventricular activity during a given session of determining if intact AV conduction is present.

44. The IMD of claim 42, wherein the means for determining if intact AV conduction is present will permit multiple, non-sequential A—A intervals to transpire without ventricular activity during a given session of checking for intact AV conduction.

45. The IMD of claim 40, wherein the means for determining if intact AV conduction is present will permit an A—A interval to transpire without ventricular activity while operating in the DDD pacing mode and determining if intact AV conduction is present.

46. The IMD of claim 25, wherein the means for determining if intact AV conduction is present includes means for inhibiting the delivery of a ventricular pace for one complete A—A interval.

47. The IMD of claim 25, wherein the means for checking for intact AV conduction periodically check for intact AV conduction while the IMD operates in the DDD pacing mode.

48. The IMD of claim 25, wherein the means for determining if intact AV conduction is present function during a first cycle operated in the DDD mode and inhibition of a ventricular pace is indicative of intact conduction.

* * * * *

UNITED STATES PATENT AND TRADEMARK OFFICE
CERTIFICATE OF CORRECTION

PATENT NO. : 7,218,965 B2 Page 1 of 1
APPLICATION NO. : 10/755454
DATED : May 15, 2007
INVENTOR(S) : Casavant et al.

It is certified that error appears in the above-identified patent and that said Letters Patent is hereby corrected as shown below:

Title Page, Item (63) change "09/413,571" to --09/746,571--

Signed and Sealed this

Eighteenth Day of September, 2007

JON W. DUDAS
*Director of the United States Patent and Trademark Office*